United States Patent [19]

Sahila et al.

[11] Patent Number: 5,194,533
[45] Date of Patent: Mar. 16, 1993

[54] TRANSITION-METAL BASED CATALYST FOR THE POLYMERIZATION AND COPOLYMERIZATION OF OLEFINS, ITS PREPARATION AND USE

[75] Inventors: Aimo Sahila, Kerava; Hilkka Knuuttila; Bill Gustafsson, both of Porvoo, all of Finland

[73] Assignee: Neste Oy, Espoo, Finland

[21] Appl. No.: 689,956

[22] Filed: Apr. 23, 1991

[30] Foreign Application Priority Data

Apr. 26, 1990 [FI] Finland ................... 902123

[51] Int. Cl.$^5$ ............................. C08F 4/69
[52] U.S. Cl. ................... 526/129; 526/126; 526/127; 526/352; 502/117; 502/158; 556/10
[58] Field of Search .............. 526/126, 127, 129, 130

[56] References Cited

U.S. PATENT DOCUMENTS 3,324,101  6/1967  Baker et al. ............... 526/126

FOREIGN PATENT DOCUMENTS 63950    5/1983  Finland.
1025747  4/1966  United Kingdom.

*Primary Examiner*—Patrick P. Garvin
*Attorney, Agent, or Firm*—Tilton, Fallon, Lungmus & Chestnut

[57] ABSTRACT

The invention relates to a new bis(trialkylsilyl) chromate of the formula

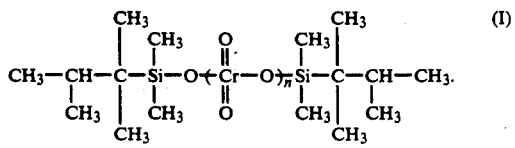

where n is approximately 1-2. Such a compound can be prepared by causing a corresponding silyl halide to react with silver chromate. The product is especially suitable for the polymerization and copolymerization of ethylene, the formed polymer having a high molar mass and a wide molar mass distribution.

6 Claims, No Drawings

TRANSITION-METAL BASED CATALYST FOR THE POLYMERIZATION AND COPOLYMERIZATION OF OLEFINS, ITS PREPARATION AND USE

The invention relates to a new bis(trialkylsilyl) chromate, to a process for its preparation, and to its use as a catalyst or catalyst component for the (co)polymerization of ethylene.

The first chromium-based catalyst for ethylene polymerization was developed by Hogan and Banks for Phillips in the mid-1950s. The catalyst is prepared by treating a silica support with chromium trioxide ($CrO_3$) in an aqueous solution, whereupon the hydroxyl groups on the surface of the silica react with the chromium trioxide and form chromate. Currently a major proportion of the world's HDPE is produced using silica-based chromium catalysts, for which reason these catalysts have been subject to a great deal of research. Attempts have been made to characterize the active center of the catalyst and the degree of oxidation of the active chromium, without, however, reaching any unambiguous result. There are evidently various types of catalytically active centers, and both Cr(II) and Cr(III) have been observed to serve as active centers in a catalyst for ethylene polymerization. Furthermore, it is possible that the active center may be di- or polynuclear.

Organosilicon chromate catalysts can also be used, either as such or affixed to the surface of various activated inorganic supports. The most important support is silica, which is calcined at a high temperature. Before polymerization, the catalysts are reduced using organometallic reducing agents, such as alkylaluminum derivatives.

U.S. Pat. No. 3,324,101 discloses an ethylene polymerization process in which ethylene is contacted with a catalytic amount of silyl chromate. The silyl chromate is preferably a bistrihydrocarbylsilyl chromate of the following formula

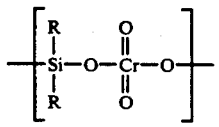

where R is a hydrocarbyl group having approximately 1-14 carbon atoms. The most preferred hydrocarbyl group was a phenyl group. The silyl chromate could be dissolved, suspended, or adsorbed onto a solid support. The most preferred support was silica. It was also advantageous to use an alkylaluminum compound as a cocatalyst.

GP Patent 1 025 747 describes ethylene polymerization by means of bis(trialkylsilyl) chromates. The patent is based on the idea that polymerization will run considerably better if the hydrocarbyl group is an alkyl instead of an aryl. In other respects this GB patent presents the same embodiments as the said U.S. patent, except that it does not suggest the adsorption of the silyl chromate onto the surface of a support. The alkyls used in the examples are methyl-, ethyl- and straight-chained propyl, butyl and hexyl groups. Another advantage offered by an alkyl group over an aryl group is that, when a bis(triphenylsilyl) chromate is used, no trialkylsiloxy group is left in the polyethylene prepared using a chromate catalyst, whereas, when a bis(triphenylsilyl) chromate is used, triphenylsiloxy groups of the catalyst are left in the polymer. The most important idea in this GB patent is, however, that bis(trialkylsilyl) chromates provide a 10-fold polymerization velocity as compared with bis(triphenylsilyl) chromates.

According to this GB publication, the bis(trialkylsilyl) chromates are prepared using a reaction between the dihydroxyl group of silanol and chromium trioxide.

FI Patent 63950 discloses for the above-mentioned U.S. patent an improvement in which the support is pretreated thermally and chemically with compounds of aluminum and titanium.

The ethylene polymers obtained using catalysts of the types mentioned above typically have a high molar mass. The melt indices are low: $MI_{2.16}=0-0.1$ and $MI_{21.6}=1-12$. A lower molar mass can be obtained by raising the polymerization temperature or by adding hydrogen into the reactor. However, in a gas phase process the raising of the temperature will cause caking of the polymer. The melt index can also be increased by the use of aluminum phenoxides for the reduction of the catalyst, whereby $MI_{2.16}$ will increase to a range of 0.3-1.0, or by a treatment with phenol before the reduction. A phenol treatment will also shorten the time it takes for the chromate to become affixed to the support, which is usually a highly time-consuming process.

The object of the invention is to provide a catalyst for the polymerization or copolymerization of olefin, preferably ethylene, the catalyst producing a polymer having a high molar mass and a wide molar mass distribution. The catalyst must also be easy to prepare and structurally so stable that it will function well in the polymerization of olefins, and in particular of ethylene. The aim is further to provide a catalyst which does not leave a phenyl group in the polymer. The catalyst must, of course, also be maximally active.

These objects of the invention have now been accomplished with a new bis(trialkylsilyl) chromate which is mainly characterized claim what is stated in the characterizing clause of Claim 1. It has thus been realized that by using the new chromate, which is a bis(dimethyl-1,1,2-trimethylpropylsilyl) chromate and/or dichromate, a polyolefin, in particular polyethylene, having a sufficient molar mass and a sufficiently wide molar mass distribution is obtained at a satisfactory polymerization velocity. The invention also relates to a process for the preparation of the above-mentioned bis(trialkylsilyl) chromate and dichromate, and to the use of the said substance as the only or an essential component in a catalyst for the polymerization or copolymerization of olefin, preferably ethylene.

The invention thus relates to a new compound of the formula

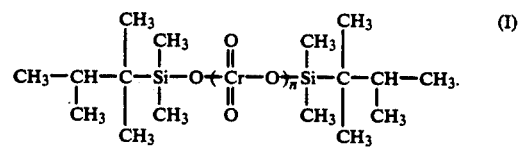

where n is approximately 1-2. The value n means that in the synthesis there is always formed some amount of dichromate (n=2), the dichromate being important in this context, since the active centers provided by it produce polymers having different molar masses and thus widen the molar mass distribution. The principal product of the synthesis is, however, bis(dimethyl-1,1,2-trimethylpropylsilyl) chromate, where n=1.

The new compound according to the invention may be prepared by a conventional reaction between silanol and chromium trioxide, but it is especially advantageous to prepare it by causing a dimethyl(1,1,2-trimethylpropyl)halogen silane of the formula

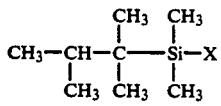

where X is a halogen, such as chlorine, to react with a silver chromate of the formula

In this case it is advantageous to use a molar ratio within the range 0.6–1.2 between the trialkylhalogen silane and the silver chromate. This is based on the fact that a stoichiometric excess of silver chromate will increase the proportion of dichromate in the product, whereupon a product having a wider molar mass distribution will be obtained using the catalyst formed.

The invention also relates to the use of the bis(trialkylsilyl) chromate of Formula (I) as the only or an essential component in a catalyst for the polymerization or copolymerization of olefin, preferably ethylene. Thus the new chromate catalyst can be used as such, for example in solution or in suspension, but it is preferred to adsorb it onto an inorganic support in order to form an effective (co)polymerization catalyst. One effective inorganic support is silica, which is preferably pretreated thermally and/or chemically. The voids volume of the initial-substance silica may be, for example, 1.55–2.0 ml/g and particle size approximately $10-85 \times 10^{-6}$ m. The thermal treatment may take place in one or several steps, in which case the temperature profile usually begins with a temperature which removes the free water from the voids in the silica at a moderate speed. The final activation of the silica is then carried out by heating the dried silica to a temperature of approximately 600°–1,000° C.

The actual adsorption is then carried out by treating the possibly activated support with a solution of bis(dimethyl-1,1,2-trimethylpropylsilyl) chromate and dichromate. The solvent used is preferably toluene. The adsorption is often carried out at a slightly elevated temperature, for example at 40° C., and its duration is in general more than one hour, for example 2 hours.

A chromate catalyst, as such or adsorbed onto a support, may be reduced, for example, by means of an organometallic compound. One suitable organometallic compound is an organoaluminum compound, preferably a compound of the formula

where R' is an alkyl, n is 1–3, and Y is a halogen or an alkoxide.

In the present invention there has thus been prepared a new type of bis(trialkylsilyl) chromate, which is more stable because one of the alkyl groups of silicon is larger in size. Furthermore, in the synthesis of the chromate also dichromate is formed, usually approximately 10%; when affixed to a support, this dichromate forms a polymerization center different from that formed by monochromate. When the chromate catalyst is prepared and it is used for the polymerization of ethylene, a polyethylene having a very wide molar mass distribution is obtained. A wide molar mass distribution is often manifested in that two peaks can be observed in the gel chromatography curve of the polymer.

By the use of supported catalysts prepared from bis(dimethyl-1,1,2-trimethylpropylsilyl) chromate (and dichromate), a wide molar mass distribution was obtained, which was due to the fact that also very large molecules were formed in the polymerization. The mean molar mass, melt index ratio, and polydispersity obtained with these catalysts are higher than those obtained with catalysts prepared using bis(triphenylsilyl) chromate (commercial state of the art) or bis(triphenylmethyl) chromate. With the catalyst according to the invention, a polyethylene was obtained which had a bimodal molar mass distribution, i.e. the distribution curve had two peaks.

Since a proportion of the chromate synthesis product according to the invention is dichromate, it seems to be precisely dichromate that produces in the catalyst active polymerization centers different from those produced by monochromate. Thus the molar mass distribution widens as the different active centers behave kinetically in different ways.

A number of embodiment examples are presented below in order to illustrate the invention.

EXAMPLE 1

Preparation of bis(dimethyl-1,1,2-trimethylpropylsilyl) chromate

The chromate may be prepared by starting from chromium trioxide and silanol or chromate or chloride. In this work, all of the syntheses were carried out shielded from light, since it has been observed that corresponding compounds decompose in UV light. The reaction products were stored in darkness. It was observed that the chromates also decompose under the effect of heat.

The synthesis used is based on the following reaction.

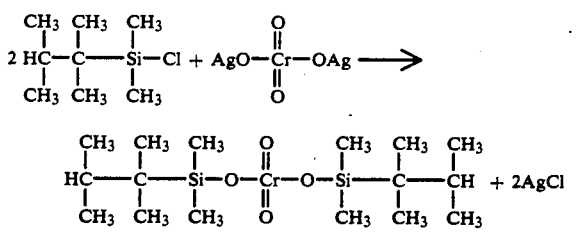

Bis(dimethyl-1,1,2-trimethylpropylsilyl) chromate, i.e. TDS-chromate, was prepared in a three-necked flask with motor stirring. Nitrogen was used as a shield gas in order to prevent the hydrolysis of the product.

14.0 g ($4.2 \times 10^{-2}$ mol) of silver chromate ($Ag_2CrO_4$) was weighed in a nitrogen cupboard into a 500-ml three-necked flask. 7.7 ml=7.0 g ($3.9 \times 10^{-2}$ mol) of dimethyl-1,1,2-trimethylpropylsilyl chloride (TDS-chloride) was measured, also in a nitrogen cupboard, into a 50-ml septum flask. The reaction apparatus was assembled and it was nitrogenized via the free neck and a drop funnel for approximately half an hour. Meanwhile, 20 ml of carbon tetrachloride was added into the septum flask.

100 ml of dried and nitrogenized carbon tetrachloride was added into the flask which contained the silver chromate, the TDS-chloride solution was injected into the drop funnel. The stirrer was started, and the reaction was initiated by adding the TDS-chloride solution into the flask slowly, in drops, in the course of approximately half an hour. The reaction was allowed to take place at room temperature and shielded from light, for 100 hours.

The chromate which had dissolved in carbon tetrachloride was filtered and dried. The yield of a syrupy, dark red product was 6.0 g, the theoretical yield being 7.9 g.

Identification of the bis(dimethyl-1,1,2-trimethylpropylsilyl) chromate

The amounts of carbon, hydrogen and chromium were determined in the elementary analysis. The amount of chromium was one-half of that which should be found in chromate. However, chlorine was present in an amount of only 2.6% by weight, i.e. TDS-chloride could not be present in such an amount that it would explain the too low an amount of chromium. Chlorine was determined using a Dionex 10 ion chromatograph. The IR spectrum has Cr-O absorptions at 990 cm$^{-1}$ and 970 cm$^{-1}$. In addition, at 1,020 cm$^{-1}$ and 1,100 cm$^{-1}$ there are strong absorptions, which were interpreted as being due to bonds between silicon and oxygen.

A mass spectrum of TDS-chromate in a carbon tetrachloride solution was run using a VG-TRIO-2-quadrupole mass spectrometer with direct feed. From the mass spectrum it could be observed that the sample contained TDS-chromate (403 m/e) and additionally TDS-dichromate (502 m/e), which was present in an amount approximately 10% of the amount of TDS-chromate. In addition, at 302 m/e there was a strong peak which could be due to dimethyl-1,1,2-trimethylpropyl siloxane.

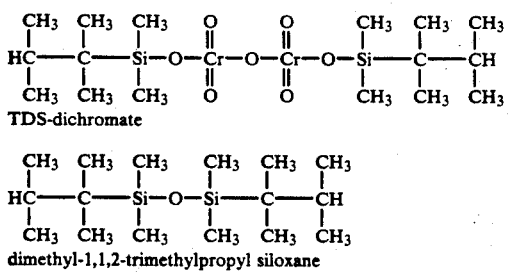

TDS-dichromate dimethyl-1,1,2-trimethylpropyl siloxane $^1$HNMR-spectra of TDS-chromate in carbon tetrachloride and of TDS-chloride were run by means of a continuous-excited Jeol 60 PMSi-NMR spectrometer using TMS as a reference. The spectrum of TDS-Cl has absorptions due to four different protons. The singlet at 0.4 ppm belongs to the six protons of the methyl groups of silicon. The rest of the absorptions fall at 0.9-1.0 ppm, and they are due to two different methyl groups, of which one causes a singlet and the other is a doublet linked by a lone proton. There is also a singlet of a lone proton within the above-mentioned region.

Three different methyl groups of silicon can be seen in the $^1$HNMR spectrum of the TDS-chromate. There is a weak singlet of the TDS-Cl methyl group at 0.4 ppm. In addition, at 0.06 and 0.26 ppm there are strong singlets, which were identified by allowing the TDS-chromate to decompose in sunlight. The absorption at 0.26 ppm decreased as compared with that at 0.06 ppm, and thus it must have been caused by chromate. It was observed that TDS-chromate decomposed under the effect of UV light, as could be presumed on the basis of the literature. When a sample placed between KBr tablets was stored in light, the IR spectrum changed. Within three days the absorption bands caused by the CR-O bond at 990 cm$^{-1}$ and 970 cm$^{-1}$ clearly decreased. The spectrum of the decomposition product considerably resembled the spectrum of polydimethyl siloxane.

EXAMPLE 2

The synthesis of chromate was repeated as in Example 1, except that smaller amounts of starting substances and a shorter reaction time (30 h) were used. The yield of the synthesis was used in its entirety for the preparation of catalyst.

EXAMPLE 3

Chromate was prepared in the same manner as in Example 1. It was identified by mass spectrometry, and the product of the synthesis was observed to be the same as in Example 1 and to contain the same proportion of dichromate. Heptane was used instead of toluene as the solvent in the preparation of the catalyst.

Preparation of supported catalysts

The support used for the catalysts mentioned above was Grace silica (SiO$_2$, silica gel), grade 955, having a voids volume of 1.55-2.00 ml/g and a particle size of approximately 10-85×10$^{-6}$ m. The water bound to the silica was removed in a quartz tube which was heated in an oven in two steps. First the temperature of the oven was raised to 200° C., whereby the physically bound water present in the voids was removed; most of the water present in silica consists of such water. Thereafter a proportion of the hydroxyl groups on the silica surface was removed at 800° C.

Conventional Schlenk technology was used for the preparation of the catalyst. Silica activated in a nitrogen cupboard and chromate were weighed into a Schlenk flask which had been rinsed with acetone and been dried in an autoclave, and a magnetic stirrer was added. The flask was closed with a septum cap, was taken out of the cupboard, and was connected to a Schlenk line. A vacuum was induced in the hose between the line and the flask, and argon was let in alternately several times, whereby an inert atmosphere was produced also in the connecting hose.

The teflon tap of the Schlenk flask was opened, whereby the flask was connected to the gas line. Toluene was added into the flask through the septum cork by using a Hamilton gastight injector, in an amount just sufficient to form a slurry in which the magnetic stirrer rotated. By this time the voids volume of the silica was filled to a slight excess. The solvent used was toluene, since it was observed that chromates dissolved better in toluene than in pentane and in hexane. The toluene had been dried on a 10 Å molecular screen for 24 h, it had been nitrogenized and thereafter degassed.

In the degassing, the solvent is frozen rapidly in liquid nitrogen, and thereafter a vacuum is induced in which the oxygen becomes detached. This is repeated several times by allowing the solvent to melt between times.

The chromate was allowed for two hours at 40° C. to become affixed to the surface of the silica. The magnetic stirring was in operation throughout this time. The flask was allowed to cool to room temperature, and the catalyst was dried in vacuum into a cold trap by opening the tap of the Schlenk flask somewhat so that the toluene was slowly distilled off.

The supported catalysts were further reduced using triethylaluminum (TEA) diluted to 10 percent in pentane. The TEA was also added slowly in drops through the septum cap by means of a Hamilton injector. Thereafter, dried and degassed pentane was further added in such an amount that the voids volume of the silica was barely filled. The reduction was observed from the change of color of the catalyst. Unreduced Cr(VI) is yellow in color, and reduced catalyst is green. After the addition of TEA, the catalyst was further agitated at room temperature for one hour and was dried.

Polymerizations

The testing of the catalysts took place in a 3-liter bench reactor equipped with a motor stirrer. The reaction took place under a pressure of 1,500 kPa and at a temperature of 95° C. Under these conditions the formed polymer is solid. The ethylene was fed from a gas flask through purification catalysts and a flowmeter into the reactor. By means of the flowmeter it was possible to observe the consumption of ethylene. The reactor was surrounded by a 0.5-liter jacket; the reactor temperature was regulated by means of cold or hot water fed into the jacket. 1.8 liters of pentane was added into the cooled reactor. Thereafter the desired amount of catalyst was added.

The temperature was raised to 95° C., and polymerization was started by opening the ethylene line to the reactor. The pressure rose to 1,500 kPa in approximately two minutes, whereafter the activity of the catalyst could be observed on the basis of ethylene consumption. The induction time of these catalysts was approximately 10-20 minutes, during which the consumption of ethylene was minor. Thereafter the consumption increased and leveled out, remaining almost constant. From the consumption of ethylene, the polymerization time was estimated, and this was in general 60-90 minutes.

The polymerization was terminated by closing the ethylene line and by cooling the reactor. Excess pressure was released into the outlet line, the reactor was opened, and the pentane, and the polymer in it, was poured into an open vessel. Antioxidant was added into this. The pentane evaporated from the vessel overnight in a draught cupboard.

Table 1 shows the results of Examples 1-3, the columns showing, from the left, the chromium content of the catalyst, the polymerization time, the yield of polymer, and the activity of the catalyst. In Example 1, two experiments, indicated by 1A and 1B, were carried out using the catalyst.

Table 2 shows the properties of the polymers prepared according to the examples; the first two columns show the melt indices, the third column their ratio, the fourth column the numerical molar mass, the fifth column the weight mean molar mass, and the sixth column the polydispersity, i.e. the ratio of the weight mean molar mass to the numerical mean molar mass.

TABLE 1

| Example | Catalyst Cr (wt. %) | Polymerization Time (min.) | Yield (g) | Activity (g/g/h) |
|---|---|---|---|---|
| 1A | 1.0 | 60 | 97 | 46 |
| 1B | 1.0 | 60 | 85 | 41 |
| 2 | 0.86 | 240 | 53 | 12 |
| 3 | 1.0 | 60 | | |

TABLE 2

| Example | MFR 27,6/5 | Mn (× 1000) | Mw (× 1000) | D |
|---|---|---|---|---|
| 1A | 37.2 | 9.1 | 408 | 45 |
| 1B | 33.2 | 10.5 | 430 | 45 |
| 2 | 36.7 | 6.1 | 415 | 68 |
| 3 | 26.5 | 6.3 | 80.1 | 12.8 |

What is claimed is:

1. A process for polymerizing a olefin by contacting the olefin under polymerization conditions with a catalyst which is a bis(trialkylsilyl) chromate of a formula

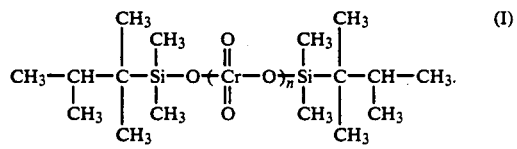

where n is approximately 1-2.

2. The process according to claim 1, wherein the bis(trialkylsilyl) chromate is adsorbed onto an inorganic support in order to form a polymerization or copolymerization catalyst.

3. The process according to claim 2, wherein the inorganic support is silica which has been pretreated thermally and/or chemically.

4. The process according to claim 1, 2 or 3 wherein a reducing compound, e.g. an organometallic compound, is used as a cocatalyst of the said polymerization or copolymerization catalyst.

5. The process according to claim 4, wherein the organometallic compound is a compound of the formula $$R_n'AlY_{3-n}$$

where R' is an alkyl and Y is a halogen or an alkoxide, and n is 1-3.

6. The process according to claim 1, wherein ethylene is the olefin to be polymerized.

* * * * *

UNITED STATES PATENT AND TRADEMARK OFFICE
CERTIFICATE OF CORRECTION

PATENT NO. : 5,194,533

DATED : March 16, 1993

INVENTOR(S) : Sahila et al.

It is certified that error appears in the above-identified patent and that said Letters Patent is hereby corrected as shown below:

Column 1, line 55, delete "GP" and add "GB"

Signed and Sealed this

Thirtieth Day of November, 1993

Attest:

BRUCE LEHMAN

Attesting Officer

Commissioner of Patents and Trademarks